United States Patent
Surnilla et al.

(10) Patent No.: US 9,719,448 B2
(45) Date of Patent: Aug. 1, 2017

(54) METHODS AND SYSTEMS FOR ADJUSTING HEATER POWER OF AN OXYGEN SENSOR TO REDUCE DEGRADATION FROM WATER

(71) Applicant: Ford Global Technologies, LLC, Dearborn, MI (US)

(72) Inventors: Gopichandra Surnilla, West Bloomfield, MI (US); Michael McQuillen, Warren, MI (US); Daniel A. Makled, Dearborn, MI (US); Richard E. Soltis, Saline, MI (US); Stephen B. Smith, Livonia, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 347 days.

(21) Appl. No.: 14/326,385

(22) Filed: Jul. 8, 2014

(65) Prior Publication Data
US 2015/0076134 A1  Mar. 19, 2015

Related U.S. Application Data

(60) Provisional application No. 61/877,853, filed on Sep. 13, 2013.

(51) Int. Cl.
*F02B 29/04*  (2006.01)
*F02D 41/14*  (2006.01)
(Continued)

(52) U.S. Cl.
CPC ....... *F02D 41/1494* (2013.01); *F02D 41/222* (2013.01); *G01N 15/0656* (2013.01); *G01N 27/4067* (2013.01); *G01N 27/4077* (2013.01); *F02D 41/144* (2013.01); *F02D 41/1454* (2013.01); *H05B 1/0236* (2013.01)

(58) Field of Classification Search
None
See application file for complete search history.

(56) References Cited

U.S. PATENT DOCUMENTS 4,611,562 A * 9/1986 Nakano ............... F02D 41/1494
123/697
5,497,655 A * 3/1996 Gee ..................... F02D 41/1494
60/272

(Continued)

FOREIGN PATENT DOCUMENTS

JP 2003083152 A * 3/2003

OTHER PUBLICATIONS

Jammoussi, Hassene et al., "Exhaust Gas Sensor Diagnosis and Controls Adaptation," U.S. Appl. No. 13/779,349, filed Feb. 27, 2013, 45 pages.

(Continued)

*Primary Examiner* — Joseph M Pelham
(74) *Attorney, Agent, or Firm* — Julia Voutyras; McCoy Russell LLP

(57) ABSTRACT

Methods and systems are provided for adjusting heater power of an oxygen sensor. In one example, a method for an engine includes adjusting heater power of a heating element of the oxygen sensor when the heater power increases by a threshold amount. The method includes subsequently increasing heater power back to a baseline power level responsive to a temperature of the heating element.

17 Claims, 4 Drawing Sheets

(51) Int. Cl.
*F02D 41/22* (2006.01)
*G01N 27/407* (2006.01)
*G01N 15/06* (2006.01)
*G01N 27/406* (2006.01)
*H05B 1/02* (2006.01)

(56) References Cited

U.S. PATENT DOCUMENTS

| | | | | |
|---|---|---|---|---|
| 5,547,552 | A * | 8/1996 | Hasegawa | G01N 27/4065 204/401 |
| 6,476,364 | B1 * | 11/2002 | Shimamura | G01N 27/4067 123/697 |
| 6,889,536 | B2 * | 5/2005 | Sakai | G01N 27/4071 73/114.72 |
| 7,114,325 | B2 * | 10/2006 | Surnilla | F01N 3/0871 204/406 |
| 7,968,827 | B2 * | 6/2011 | Adams | F02D 41/1494 123/672 |
| 8,438,899 | B2 * | 5/2013 | Zawacki | F02D 41/1494 701/30.9 |
| 2002/0078938 | A1 * | 6/2002 | Hada | F02D 41/1494 123/697 |
| 2003/0178016 | A1 * | 9/2003 | Nebiyeloul-Kifle | F02D 41/1494 123/676 |
| 2005/0000504 | A1 * | 1/2005 | Ohkuma | F02D 41/1494 123/680 |
| 2005/0006368 | A1 * | 1/2005 | Sell | H05B 1/0236 219/202 |
| 2007/0125348 | A1 * | 6/2007 | Aoki | F02D 35/0023 123/676 |
| 2008/0184774 | A1 * | 8/2008 | Aoki | F02D 41/1494 73/23.32 |
| 2009/0319085 | A1 * | 12/2009 | Sell | F02D 41/1494 700/275 |
| 2011/0047985 | A1 * | 3/2011 | Zawacki | F02D 41/1494 60/286 |
| 2012/0055234 | A1 * | 3/2012 | Yonezu | G01N 27/4077 73/31.05 |
| 2015/0034484 | A1 * | 2/2015 | Nakasone | G01N 27/4162 204/412 |
| 2015/0057910 | A1 * | 2/2015 | Surnilla | F02M 26/44 701/108 |
| 2015/0114346 | A1 * | 4/2015 | Surnilla | F02D 41/0007 123/349 |
| 2015/0168261 | A1 * | 6/2015 | Day | B05D 1/18 73/114.73 |
| 2016/0139073 | A1 * | 5/2016 | Mcquillen | G01N 27/4067 205/784.5 |
| 2016/0169138 | A1 * | 6/2016 | McQuillen | G02D 41/1494 219/497 |

OTHER PUBLICATIONS

Surnilla, Gopichandra et al., "Method for Estimating Charge Air Cooler Condensation Storage and/or Release with an Intake Oxygen Sensor," U.S. Appl. No. 13/967,968, filed Aug. 15, 2013, 57 pages.

Surnilla, Gopichandra et al., "Methods and Systeems for Indicating Water at an Oxygen Sensor Based on Sensor Heater Power Consumption," U.S. Appl. No. 13/971,714, filed Aug. 20, 2013, 32 pages.

* cited by examiner

METHODS AND SYSTEMS FOR ADJUSTING HEATER POWER OF AN OXYGEN SENSOR TO REDUCE DEGRADATION FROM WATER

CROSS REFERENCE TO RELATED APPLICATIONS

The present application claims priority to U.S. Provisional Patent Application No. 61/877,853, "METHODS AND SYSTEMS FOR ADJUSTING HEATER POWER OF AN OXYGEN SENSOR TO REDUCE DEGRADATION FROM WATER," filed on Sep. 13, 2013, the entire contents of which are hereby incorporated by reference for all purposes.

BACKGROUND/SUMMARY

Engine systems may utilize one or more gas constituent sensors, such as oxygen sensors, for sensing an oxygen concentration of air flowing through engine air passages. In one example, an engine system may include one or more intake oxygen sensors (IAO2) located in the engine intake. For example, an intake oxygen sensor may be positioned in an intake passage, downstream from a compressor and a charge air cooler, to provide an indication of EGR flow. In another example, the engine system may include one or more exhaust gas sensors in an exhaust system of the engine system to detect an air-fuel ratio of exhaust gas exhausted from the engine. Under certain engine operating conditions, such as a cold start or condensate formation, water may splash against and contact the oxygen sensor. When water contacts the oxygen sensor the temperature of the sensor decreases. As a result, heater power of a heating element of the oxygen sensor increases to increase the sensor temperature. When the heater power increases for an extended period of time when water is on the oxygen sensor, the heating element may crack, thereby degrading the oxygen sensor.

In one example, the issues described above may be addressed by a method for adjusting heater power of a heating element of an oxygen sensor in response to an increase in the heater power by a threshold amount. Water droplets may be indicated at the oxygen sensor when the heater power increases above a baseline power level by the threshold level. In this way, heater power may be adjusted to reduce degradation of the heating element of the oxygen sensor due to water at the sensor.

As one example, heater power of the heating element of the oxygen sensor may be decreased responsive to water contacting the heating element. In one example, water contacting the heating element may be indicated when the heater power increases above a baseline power level by a threshold amount. In another example, water contacting the heating element may be indicated when a pumping current of the oxygen sensor decreases by a threshold pumping current amount. In some examples, decreasing the heater power may include turning off the power of the heating element. After a duration of decreasing the heater power, the heater power may be turned back on and increased to the baseline power level. The duration may either be predetermined or based on when a temperature of the heating element decreases below a threshold temperature, the threshold temperature being a threshold cracking temperature. In this way, reducing the heater power when water is indicated at the oxygen sensor may reduce oxygen sensor degradation via cracking of the heating element.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 2:
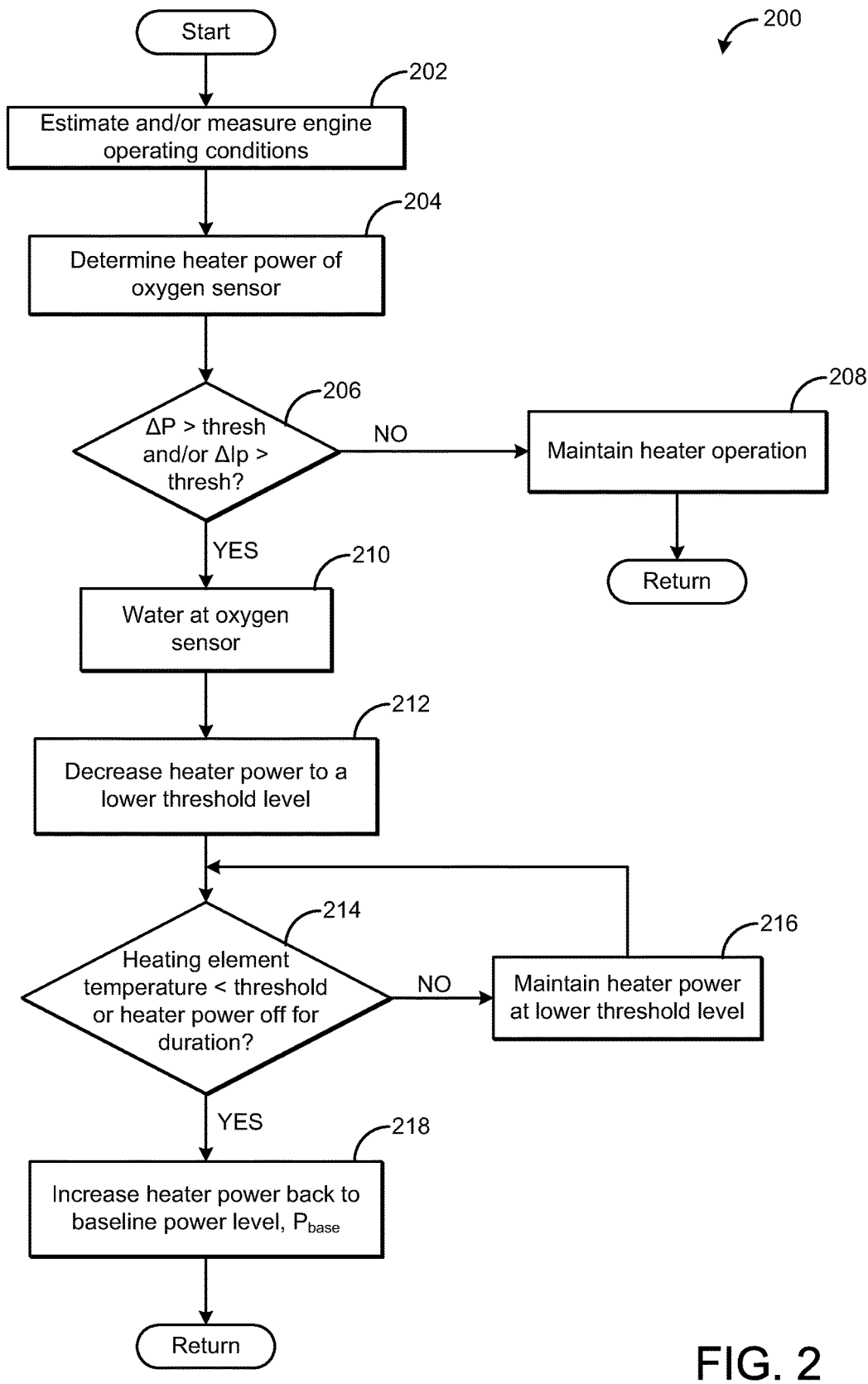
FIG. 2 is a flow chart of a method for adjusting heater power of a heating element of an oxygen sensor responsive to water at the oxygen sensor.
Figure 3:
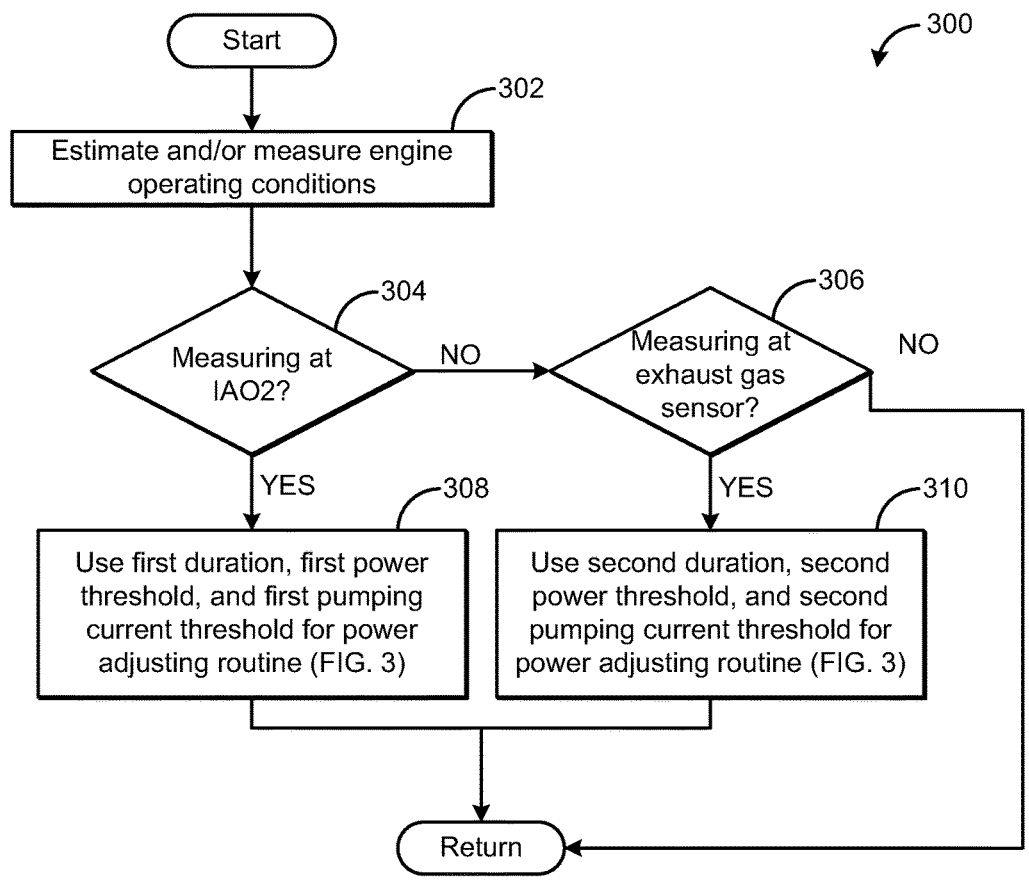
FIG. 3 is a flow chart of a method for determining parameters for a method for adjusting heater power of a heating element of an oxygen sensor based on the location of the oxygen sensor.
Figure 4:
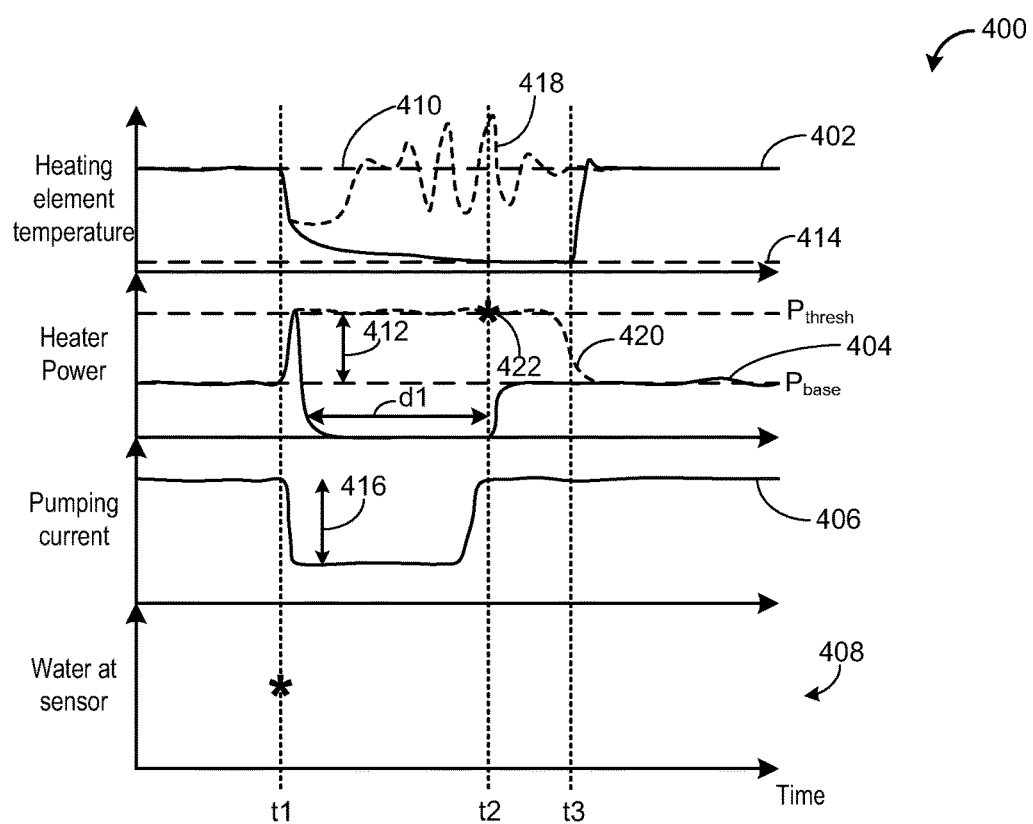
FIG. 4 is a graph of an example response of oxygen sensor operating parameters to water at the oxygen sensor.

The following description relates to systems and methods for adjusting heater power of an oxygen sensor. An engine system, such as the engine system of FIG. 1, may include one or more oxygen sensors. In one example, an intake oxygen sensor may be positioned in an intake passage of the engine. In another example, an exhaust oxygen sensor may be positioned in an exhaust passage of the engine. The one or more oxygen sensors each include a heating element with adjustable heater power. When water contacts the heating element of the oxygen sensor, the heater power may increase. If the heater power is maintained at the increased level, the heating element may crack, thereby causing oxygen sensor degradation. In some examples, as shown at FIGS. 2-3, a method may include adjusting heater power based on an indication of water at the oxygen sensor. In some examples, the heater power may be reduced responsive to an initial increase in heater power and/or a decrease in pumping current of the oxygen sensor indicative of water splashing against the sensor. Example adjustments to heater power responsive to water splash conditions are shown at FIG. 4. By decreasing the heater power for a duration when water is indicated at the oxygen sensor, oxygen sensor degradation may be reduced.

Figure 1:
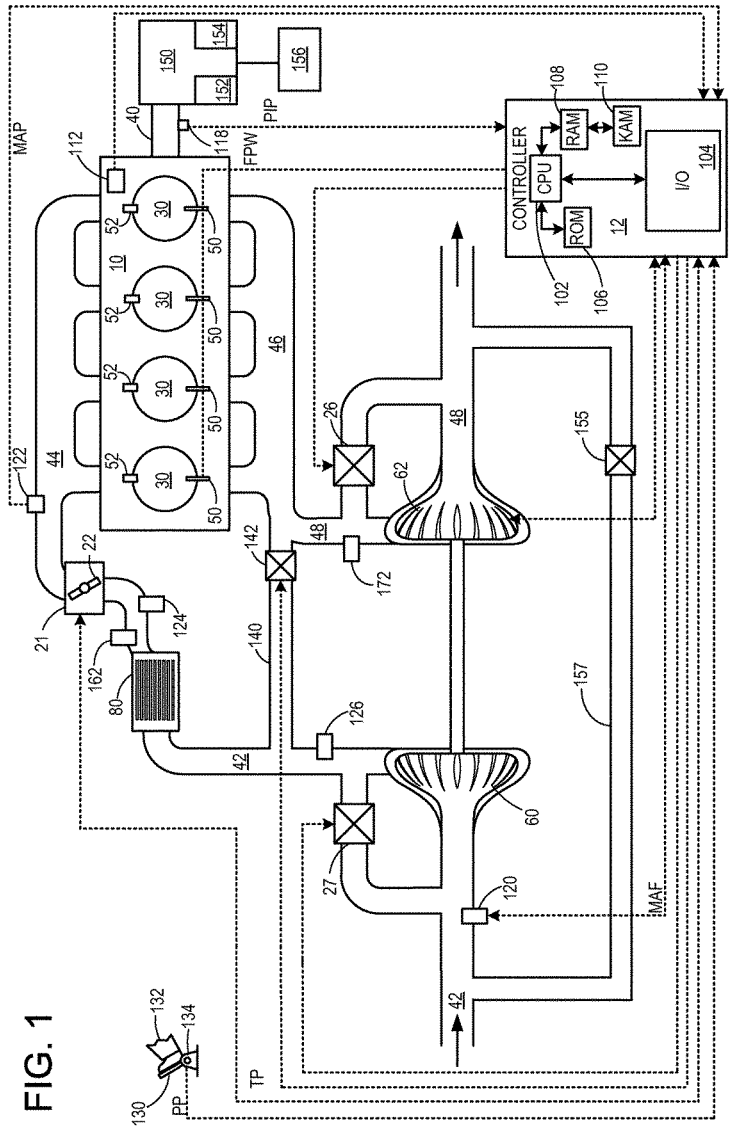
FIG. 1 is a schematic diagram of an example engine system including one or more oxygen sensors.

FIG. 1 is a schematic diagram showing an example engine 10, which may be included in a propulsion system of an automobile. The engine 10 is shown with four cylinders or combustion chambers 30. However, other numbers of cylinders may be used in accordance with the current disclosure. Engine 10 may be controlled at least partially by a control system including a controller 12, and by input from a vehicle operator 132 via an input device 130. In this example, the input device 130 includes an accelerator pedal and a pedal position sensor 134 for generating a proportional pedal position signal PP. Each combustion chamber (e.g., cylinder) 30 of the engine 10 may include combustion chamber walls with a piston (not shown) positioned therein. The pistons may be coupled to a crankshaft 40 so that reciprocating motion of the piston is translated into rotational motion of the crankshaft. The crankshaft 40 may be coupled to at least one drive wheel of a vehicle via an intermediate transmission system 150. Further, a starter motor may be coupled to crankshaft 40 via a flywheel to enable a starting operation of engine 10. The crankshaft 40 may also be used to drive an alternator (not shown in FIG. 1).

An engine output torque may be transmitted to a torque converter (not shown) to drive the automatic transmission system 150. Further, one or more clutches may be engaged, including forward clutch 154, to propel the automobile. In one example, the torque converter may be referred to as a component of the transmission system 150. Further, transmission system 150 may include a plurality of gear clutches 152 that may be engaged as needed to activate a plurality of fixed transmission gear ratios. Specifically, by adjusting the engagement of the plurality of gear clutches 152, the transmission may be shifted between a higher gear (that is, a gear with a lower gear ratio) and a lower gear (that is, a gear with a higher gear ratio). As such, the gear ratio difference enables a lower torque multiplication across the transmission when in the higher gear while enabling a higher torque multiplication across the transmission when in the lower gear. The vehicle may have four available gears, where transmission gear four (transmission fourth gear) is the highest available gear and transmission gear one (transmission first gear) is the lowest available gear. In other embodiments, the vehicle may have more or less than four available gears. A controller may vary the transmission gear (e.g., upshift or downshift the transmission gear) to adjust an amount of torque conveyed across the transmission and torque converter to vehicle wheels 156 (that is, an engine shaft output torque).

As the transmission shifts to a lower gear, the engine speed (Ne or RPM) increases, increasing engine airflow. An intake manifold vacuum generated by the spinning engine may be increased at the higher RPM. In some examples, downshifting may be used to increase engine airflow and purge condensate built up in a charge air cooler (CAC) 80.

The combustion chambers 30 may receive intake air from the intake manifold 44 and may exhaust combustion gases via an exhaust manifold 46 to an exhaust passage 48. The intake manifold 44 and the exhaust manifold 46 can selectively communicate with the combustion chamber 30 via respective intake valves and exhaust valves (not shown). In some embodiments, the combustion chamber 30 may include two or more intake valves and/or two or more exhaust valves.

Fuel injectors 50 are shown coupled directly to the combustion chamber 30 for injecting fuel directly therein in proportion to the pulse width of signal FPW received from controller 12. In this manner, the fuel injector 50 provides what is known as direct injection of fuel into the combustion chamber 30; however it will be appreciated that port injection is also possible. Fuel may be delivered to the fuel injector 50 by a fuel system (not shown) including a fuel tank, a fuel pump, and a fuel rail.

In a process referred to as ignition, the injected fuel is ignited by known ignition means such as spark plug 52, resulting in combustion. Spark ignition timing may be controlled such that the spark occurs before (advanced) or after (retarded) the manufacturer's specified time. For example, spark timing may be retarded from maximum break torque (MBT) timing to control engine knock or advanced under high humidity conditions. In particular, MBT may be advanced to account for the slow burn rate. In one example, spark may be retarded during a tip-in. In an alternate embodiment, compression ignition may be used to ignite the injected fuel.

The intake manifold 44 may receive intake air from an intake passage 42. The intake passage 42 includes a throttle 21 having a throttle plate 22 to regulate flow to the intake manifold 44. In this particular example, the position (TP) of the throttle plate 22 may be varied by the controller 12 to enable electronic throttle control (ETC). In this manner, the throttle 21 may be operated to vary the intake air provided to the combustion chambers 30. For example, the controller 12 may adjust the throttle plate 22 to increase an opening of the throttle 21. Increasing the opening of the throttle 21 may increase the amount of air supplied to the intake manifold 44. In an alternate example, the opening of the throttle 21 may be decreased or closed completely to shut off airflow to the intake manifold 44. In some embodiments, additional throttles may be present in intake passage 42, such as a throttle upstream of a compressor 60 (not shown).

Further, in the disclosed embodiments, an exhaust gas recirculation (EGR) system may route a desired portion of exhaust gas from the exhaust passage 48 to the intake passage 42 via an EGR passage, such as high pressure EGR passage 140. The amount of EGR provided to the intake passage 42 may be varied by the controller 12 via an EGR valve, such as high pressure EGR valve 142. Under some conditions, the EGR system may be used to regulate the temperature of the air and fuel mixture within the combustion chamber. FIG. 1 shows a high pressure EGR system where EGR is routed from upstream of a turbine of a turbocharger to downstream of a compressor of a turbocharger through EGR passage 140. FIG. 1 also shows a low pressure EGR system where EGR is routed from downstream of turbine of a turbocharger to upstream of a compressor of a turbocharger through low pressure EGR passage 157. A low pressure EGR valve 155 may control the amount of EGR provided to the intake passage 42. In some embodiments, the engine may include both a high pressure EGR and a low pressure EGR system, as shown in FIG. 1. In other embodiments, the engine may include either a low pressure EGR system or a high pressure EGR system. When operable, the EGR system may induce the formation of condensate from the compressed air, particularly when the compressed air is cooled by the charge air cooler, as described in more detail below.

The engine 10 may further include a compression device such as a turbocharger or supercharger including at least a compressor 60 arranged along the intake passage 42. For a turbocharger, the compressor 60 may be at least partially driven by a turbine 62, via, for example a shaft, or other coupling arrangement. The turbine 62 may be arranged along the exhaust passage 48. Various arrangements may be provided to drive the compressor. For a supercharger, the compressor 60 may be at least partially driven by the engine and/or an electric machine, and may not include a turbine. Thus, the amount of compression provided to one or more cylinders of the engine via a turbocharger or supercharger may be varied by the controller 12.

In the embodiment shown in FIG. 1, the compressor 60 may be driven primarily by the turbine 62. The turbine 62 may be driven by exhaust gases flowing through the exhaust passage 48. Thus, the driving motion of the turbine 62 may drive the compressor 60. As such, the speed of the compressor 60 may be based on the speed of the turbine 62. As the speed of the compressor 60 increases, more boost may be provided through the intake passage 42 to the intake manifold 44.

Further, the exhaust passage 48 may include a wastegate 26 for diverting exhaust gas away from the turbine 62. Additionally, the intake passage 42 may include a compressor bypass or recirculation valve (CRV) 27 configured to divert intake air around the compressor 60. The wastegate 26 and/or the CRV 27 may be controlled by the controller 12 to be opened when a lower boost pressure is desired, for example. For example, in response to compressor surge or a potential compressor surge event, the controller 12 may open the CBV 27 to decrease pressure at the outlet of the compressor 60. This may reduce or stop compressor surge.

The exhaust passage 48 may also include an exhaust gas sensor 172, such as an exhaust oxygen sensor. The exhaust gas sensor 172 may be any suitable sensor for providing an indication of exhaust gas air-fuel ratio such as a linear oxygen sensor or UEGO (universal or wide-range exhaust gas oxygen), a two-state oxygen sensor or EGO, or a HEGO (heated EGO). In some embodiments, exhaust gas sensor 172 may be a first one of a plurality of exhaust gas sensors positioned in the exhaust system. For example, additional exhaust gas sensors may be positioned downstream of the turbine 62.

The intake passage 42 may further include a charge air cooler (CAC) 80 (e.g., an intercooler) to decrease the temperature of the turbocharged or supercharged intake gases. In some embodiments, the CAC 80 may be an air to air heat exchanger. In other embodiments, the CAC 80 may be an air to liquid heat exchanger. The CAC 80 may also be a variable volume CAC. Hot charge air (boosted air) from the compressor 60 enters the inlet of the CAC 80, cools as it travels through the CAC, and then exits to pass through the throttle 21 and then enter the engine intake manifold 44. Ambient air flow from outside the vehicle may enter engine 10 through a vehicle front end and pass across the CAC, to aid in cooling the charge air. Condensate may form and accumulate in the CAC when the ambient air temperature decreases, or during humid or rainy weather conditions, where the charge air is cooled below the water dew point temperature. Further, when the charge air entering the CAC is boosted (e.g., boost pressure and/or CAC pressure is greater than atmospheric pressure), condensate may form if the CAC temperature falls below the dew point temperature. When the charge air includes recirculated exhaust gasses, the condensate can become acidic and corrode the CAC housing. The corrosion can lead to leaks between the air charge, the atmosphere, and possibly the coolant in the case of water-to-air coolers. Further, if condensate builds up in the CAC, it may be ingested by the engine during times of increased airflow. As a result, unstable combustion and/or engine misfire may occur.

The engine 10 may further include one or more oxygen sensors positioned in the intake passage 42, or engine intake. As such, the one or more oxygen sensors may be referred to as intake oxygen sensors. In the depicted embodiment, an intake oxygen sensor (IAO2) 162 is positioned downstream of the CAC 80, in the engine intake. In one example, the IAO2 162 may be positioned at an outlet of the CAC 80. As such, the IAO2 162 may be referred to herein as the CAC outlet oxygen sensor. In another example, the IAO2 162 may be positioned downstream of the CAC 80 outlet, in the intake manifold 44. In yet another example, the IAO2 may be positioned upstream of the throttle 21 and downstream of the CAC 80.

IAO2 162 may be any suitable sensor for providing an indication of the oxygen concentration of the charge air (e.g., air flowing through the intake passage 42), such as a linear oxygen sensor, intake UEGO (universal or wide-range exhaust gas oxygen) sensor, two-state oxygen sensor, etc. During operation, a pumping current of the intake oxygen sensor may be indicative of an amount of oxygen in the gas flow.

The IAO2 162 includes a heater, or heating element, configured to be activated in order to heat the IAO2 to its operating temperature. Specifically, the IAO2 may have a set point temperature such as 800° C. In another example, the set point temperature of the IAO2 may be greater or less than 800° C. A closed loop control system of the IAO2 may then control the heating element to maintain the set point temperature. For example, if the temperature of the sensor decreases below the set point, the heating element may consume more power output by the sensor in order to increase the sensor temperature. Said another way, in response to the temperature of the sensor decreasing below the set point, heater power of the heating element may increase above a base level. Further details on adjusting heater power of the heating element to maintain a set point temperature of the IAO2 is discussed below. The exhaust gas sensor 172 may also include a heater, or heating element, as described above with regard to the IAO2 162.

The EGR dilution percentage of the intake charge at a given time (e.g., the proportion of combusted gases to air in an intake passage of the engine) may be inferred from the output of the IAO2 162. In particular, when oxygen intake concentration is reduced, an increase in EGR may be inferred since the presence of EGR may dilute oxygen in the intake stream at the IAO2 sensor 162. Conversely, when oxygen intake concentration increases, a decrease in EGR may be inferred due to a reduction of EGR. Controller 12 may estimate the percent dilution of the EGR flow based on feedback from IAO2 162. Further, the controller 12 may then estimate an EGR amount or EGR flow rate based on feedback from the IAO2 162. In some examples, the controller 12 may then adjust one or more of high pressure EGR valve 142, low pressure EGR valve 155, throttle 21, CRV 27, and wastegate 26 to achieve a desired EGR dilution percentage of the intake charge and/or desired EGR flow rate.

The controller 12 is shown in FIG. 1 as a microcomputer, including microprocessor unit 102, input/output ports 104, an electronic storage medium for executable programs and calibration values shown as read only memory chip 106 in this particular example, random access memory 108, keep alive memory 110, and a data bus. The controller 12 may receive various signals from sensors coupled to the engine 10 for performing various functions to operate the engine 10. In addition to those signals previously discussed, these signals may include measurement of inducted mass air flow from MAF sensor 120; engine coolant temperature (ECT) from temperature sensor 112, shown schematically in one location within the engine 10; a profile ignition pickup signal (PIP) from Hall effect sensor 118 (or other type) coupled to crankshaft 40; the throttle position (TP) from a throttle position sensor, as discussed; and absolute manifold pressure signal, MAP, from sensor 122, as discussed. Engine speed signal, RPM, may be generated by the controller 12 from signal PIP. Manifold pressure signal MAP from a manifold pressure sensor may be used to provide an indication of vacuum, or pressure, in the intake manifold 44. Note that various combinations of the above sensors may be used, such as a MAF sensor without a MAP sensor, or vice versa. During stoichiometric operation, the MAP sensor can give an indication of engine torque. Further, this sensor, along with the detected engine speed, can provide an estimate of charge (including air) inducted into the cylinder. In one example, the Hall effect sensor 118, which is also used as an engine speed sensor, may produce a predetermined number of equally spaced pulses every revolution of the crankshaft 40.

Other sensors that may send signals to controller 12 include a temperature and/or pressure sensor 124 at an outlet of a charge air cooler 80, the IAO2 162, and a boost pressure sensor 126. Other sensors not depicted may also be present, such as a sensor for determining the intake air velocity at the inlet of the charge air cooler, and other sensors. In some examples, storage medium read-only memory chip 106 may be programmed with computer readable data representing instructions executable by microprocessor unit 102 for performing the methods described below as well as other variants that are anticipated but not specifically listed. Example routines are described herein at FIGS. 2-3.

The system of FIG. 1 provides for an engine system including an intake manifold including an intake throttle, a charge air cooler positioned upstream of the intake manifold, a first oxygen sensor positioned at an outlet of the charge air cooler, the oxygen sensor including a first heating element, and a controller with computer readable instructions for turning off heater power of the first heating element in response to an indication of water contacting the first oxygen sensor. In one example, water contacting the first oxygen sensor is indicated by one or more of an increase in heater power of the first heating element above a baseline power level by a first threshold amount or a decrease in pumping current of the first oxygen sensor by a second threshold amount. The computer readable instructions further include subsequently turning on the heater power after the heater power is turned off for a duration, the duration based on one or more of an amount of time for water to evaporate from the first heating element or an amount of time to reduce a temperature of the first heating element below a threshold cracking temperature.

The system further comprises a second oxygen sensor positioned in an exhaust passage of the engine, the second oxygen sensor including a second heating element. The computer readable instructions further include instructions for turning off heater power of the second heating element in response to an indication of water contacting the second oxygen sensor. Water contacting the second oxygen sensor is indicated by one or more of an increase in heater power of the second heating element above a baseline power level by a first threshold amount or a decrease in pumping current of the second oxygen sensor by a second threshold amount. Oxygen sensors in the engine, such as exhaust oxygen sensor 172 and intake oxygen sensor 162 shown in FIG. 1, may experience water splash conditions where water contacts the sensor. For example, as shown in FIG. 1, the intake oxygen sensor (IAO2) is positioned downstream of the CAC. As discussed above, condensate may form within and then be discharged from the CAC. As result, discharged condensate may contact (e.g., splash against) the IAO2. During cold start conditions, oxygen sensors (such as UEGO sensors) in the exhaust passage may also experience water splash wherein water contacts the heating element of the oxygen sensor.

As introduced above, an oxygen sensor (exhaust or intake oxygen sensor) may include a heating element for maintaining an operating temperature of the sensor. When water contacts or splashes against the oxygen sensor the temperature of the heating element may decrease. As a result, a closed loop temperature controller of the oxygen sensor increases heater power supplied to the heating element to maintain the oxygen sensor temperature at the set point temperature. The heater power may be maintained at this higher level (e.g., higher than a baseline power level) for a period of time until the temperature of the oxygen sensor returns to the set point temperature. In one example, heater power may be increased from a baseline power level to a maximum power level responsive to water contacting the sensor. Further, when water contacts the oxygen sensor, water may fill a protection tube surrounding the heating element of the sensor. Maintaining the heater power at a higher (e.g., maximum) power level for an extended period of time while water is inside the protection tube and contacting the heating element may cause the heating element to crack. As a result, the oxygen sensor may become degraded and not be able to maintain the oxygen sensor at the required set point temperature.

In one example, heating element degradation may be reduced by controlling heater power during water splash. Specifically, a controller of the engine may reduce heater power of the oxygen sensor rather than maintaining the heater power at a higher level to increase the temperature of the oxygen sensor. For example, when water contacts the oxygen sensor, the heater power of the heating element may initially increase from a baseline power level to a second, higher (e.g., maximum) power level. In response to indication of water splash (e.g., water contact) at the oxygen sensor, the controller may reduce heater power or turn off heater power. In this way, the controller may override or disable the closed loop temperature controller of the oxygen sensor by reducing heater power and not allowing the heater power to be controlled by temperature alone. By maintaining the heater power off or at a third, lower power level (e.g., lower than the baseline power level), the heating element may not crack while water is at the oxygen sensor. After the water has evaporated from the oxygen sensor and the heating element temperature is below a threshold temperature, the heater power of the heating element may be turned back on or increased back to the baseline power level. Once the water evaporates and the heating element is turned back on, the temperature of the oxygen sensor will return (on its own) to the set point or standard operating temperature. Thus, a sustained second, higher power level of the heating element is not necessary to return the oxygen sensor to the set point temperature.

In one example, water contacting (e.g., splashing) the oxygen sensor may be indicated by an increase in the heater power of the heating element (e.g., power consumption of the heating element). Specifically, if heater power of the heating element increases by a threshold amount, water at the oxygen sensor may be indicated. In one example, a baseline power level, $P_{base}$, may be determined during calibration of the oxygen sensor. The baseline power level of the oxygen sensor may be determined during a condition wherein no water is contacting the sensor in dry or humid air (e.g., substantially dry conditions). Then, during engine operation, if the heater power increases above the baseline power level by a threshold amount, a controller (e.g., controller 12 shown in FIG. 1) may indicate water at the oxygen sensor. This concept may be described with the following formula:

$$\Delta P = P_{measured} - P_{base},$$

where $\Delta P$ is the change in heater power during sensor operation, $P_{measured}$ is the measured heater power of the heating element, and $P_{base}$ is the baseline power level of the heating element (without water contacting the sensor). If $\Delta P$ is greater than a threshold power (e.g., water splash threshold), water at the oxygen sensor may be indicated. The threshold power, or threshold amount of power increase, may be based on a threshold amount of water that may fill the protection tube surrounding the heating element or contact the heating element and cause it to crack when heater power increases. Thus, in response to the initial increase in heater power above the baseline power level, the controller may adjust heater power to reduce oxygen sensor degradation via heating element cracking.

In another example, water contacting (e.g., splashing) the oxygen sensor may be indicated by a decrease in pumping current of the oxygen sensor. As described above, the pumping current of the oxygen sensor may be indicative of an amount of oxygen in the gas flow (at the oxygen sensor). When water hits the oxygen sensor, the water splash causes water vapor surrounding the oxygen sensor to reduce the oxygen concentration. The pumping current of the oxygen sensor will decrease in response to the reduced oxygen concentration of the air flow. Thus, when the pumping current of the oxygen sensor decreases by a threshold amount, water may be indicated at the oxygen sensor. In response, the controller may adjust the heater power to reduce heating element degradation.

In this way, an engine method may include adjusting heater power of a heating element of an oxygen sensor in response to an increase in the heater power by a threshold amount. The oxygen sensor is one of an exhaust oxygen sensor positioned in an engine exhaust or an intake oxygen sensor positioned in an engine intake. The method may further include indicating water droplets at the oxygen sensor when the heater power increases above a baseline power level by the threshold amount. In one example, adjusting the heater power of the heating element includes decreasing the heater power from a first, increased level due to water droplets hitting the heating element and to a second level, the second level lower than the first level and lower than a baseline power level. In some examples, the second level is substantially zero such that the heater power is turned off.

In one example, the method further includes, after decreasing the heater power, increasing the heater power to the baseline power level in response to a temperature of the heating element decreasing below a threshold temperature, the threshold temperature based on a temperature at which the heating element may crack under water splash conditions. In another example, the method further includes, after decreasing the heater power, increasing the heater power to the baseline power level after a duration, the duration based on a time to evaporate water at the heating element and reduce a temperature of the heating element below a threshold cracking temperature. In another example, the method includes additionally or alternatively adjusting the heater power of the heating element in response to a decrease in pumping current of the oxygen sensor by a threshold amount, the threshold amount based on an oxygen concentration indicating water at the oxygen sensor.

FIG. 2 shows a method 200 for adjusting heater power of a heating element of an oxygen sensor responsive to water splash conditions at the sensor. Specifically, the oxygen sensor may be one or more of an exhaust oxygen sensor positioned in an exhaust (e.g., exhaust passage) of an engine and/or an intake oxygen sensor positioned in an intake (e.g., intake passage) of the engine. For example, the intake oxygen sensor may be positioned proximate to an outlet of a CAC (e.g., such as the intake oxygen sensor 162 shown in FIG. 1). In another example, the intake oxygen sensor may be positioned in the intake manifold of the engine.

Though the method 200 may be carried out for either type of oxygen sensor, the parameters used for initiating and executing the heater power adjusting routine in response to water splash may be different depending on where the oxygen sensor is located within the engine system. For example, the duration of reducing the heater power in response to water splash may be different for an exhaust gas sensor and an intake oxygen sensor. Further, the threshold increase in heater power or the threshold decrease in pumping current used to indicate water splash at the sensor may be different for the exhaust gas sensor and the intake oxygen sensor due to different constituents in the gas flow.

FIG. 3 shows a method 300 for determining which set of parameters should be used in method 200 based on where the oxygen sensor is located in the engine. In one example, the method 200 and the method 300 are executable by the controller 12 shown in FIG. 1. The method 300 begins at 302 by estimating and/or measuring engine operating conditions. Engine operating conditions may include engine speed and load, pedal position, mass air flow, torque demand, EGR flow, oxygen sensor measurements, conditions of the CAC (e.g., temperature and pressure), ambient temperature and pressure, etc. At 304 the method includes determining if the controller is measuring heater power at the intake oxygen sensor (IAO2). If the controller is measuring heater power at the IAO2, the method continues on to 308 to use a first duration, a first power threshold, and a first pumping current threshold when executing the power adjusting method shown at FIG. 2. The method shown at FIG. 2 may be referred to as a sensor protection routine. When running the sensor protection routine illustrated in method 200, the controller may use the first set of parameters if the method is being run for an IAO2. The first duration may be used at 214 in method 200. Additionally, the first power threshold may be the threshold power and the first pumping current threshold may be the threshold pumping current used at 206 in method 200.

Alternatively, if the controller is measuring heater power at an exhaust gas sensor (e.g., exhaust oxygen sensor), the method continues from 306 to 310 to use a second duration, a second power threshold, and a second pumping current when executing the power adjusting method shown at FIG. 2. Thus, when running the sensor protection routine illustrated in method 200, the controller may use the second set of parameter if the method is being run for an exhaust oxygen sensor. In this example, the second duration may be used at 214 in method 200. Additionally, the second power threshold may be the threshold power and the second pumping current threshold may be the threshold pumping current used at 206 in method 200.

In one example, the first duration used at 308 may be shorter or longer than the second duration used at 310. As described above, in one example, the durations for maintain heater power off or at a decreased level may be predetermined during engine testing. Thus, due to the different locations of the oxygen sensors, each sensor may require a different duration for water to evaporate for the sensor. For example, the intake oxygen sensor may be in a cooler location (e.g., downstream from the CAC) and require a first duration to evaporate water from the heating element of the oxygen sensor. Alternatively, the exhaust gas sensor may be in a warmer location (e.g., in the engine exhaust) and require a second duration to evaporate water from the heating element of the oxygen sensor, the second duration being shorter than the first location.

In alternate examples, the durations at 308 and 310 may be based on engine operating conditions such an engine temperatures. For example, during a cold start, the second duration may be longer than when the engine is fully warmed up (e.g., engine temperature and catalyst temperature are above respective threshold temperatures). Further, during conditions wherein condensate may be released from the CAC (e.g., during periods of increased air flow and/or during condensate-forming conditions), the first duration may be longer since more water may contact the IAO2 for a longer duration. Thus, the IAO2 heating element power may need to be turned off for a longer duration.

Likewise, the first power threshold and the first pumping current threshold may be higher or lower than the second power threshold and the second pumping current threshold. For example, during engine operation when the engine is fully warmed up (e.g., engine temperature and catalyst temperature are above respective threshold temperatures), the first pumping current threshold may be smaller than the second pumping current threshold. When the engine is not operating under cold start conditions and the engine is fully warmed up, water may be more likely to contact an IAO2 than an exhaust oxygen sensor. As such, the first pumping current threshold for the IAO2 may be smaller than the second pumping current threshold in order to more accurately detect when water is contacting the IAO2. In this way, a method for adjusting heater power during water splash conditions may use different parameters for an IAO2 and an exhaust gas sensor. The parameters may be based on the location of the oxygen sensor, condensate-forming conditions (e.g., ambient humidity, temperature, and pressure, as well as CAC temperatures and pressure), engine temperatures (e.g., cold start vs. fully warmed up operating conditions), gas temperatures, etc.

After determining which set of parameters to use for method 200, based on the location of the oxygen sensor, the controller may execute method 200 as shown in FIG. 2. Method 200 begins at 202 by estimating and/or measuring engine operating conditions. Engine operating conditions may include engine speed and load, pedal position, mass air flow, torque demand, EGR flow, oxygen sensor measurements, conditions of the CAC (e.g., temperature and pressure), ambient temperature and pressure, etc. At 204, the method includes determining heater power of the heating element of the oxygen sensor. Said another way, at 204, the controller may determine the amount of power consumed by the heating element. Then, at 206, the method includes determining if a change in heater power, ΔP, is greater than a threshold power and/or a change in pumping current, ΔIp, is greater than a threshold pumping current. In one example, at 206, the controller may determine if the difference between the measured heater power and the baseline power level (e.g., ΔP) of the heating element is greater than a threshold. As discussed above, the threshold may be a threshold power or threshold amount of power increase. The threshold may be based on a threshold increase in power corresponding to a threshold power level that may result in heating element degradation and cracking. Additionally, the threshold power may be based on the location of the oxygen sensor, as determined by method 300.

In another example, at 206, the controller may determine if the difference between a baseline or previous pumping current and a measured pumping current is greater than a threshold pumping current. As discussed above, in the presence of water, the pumping current of the oxygen sensor may decrease by a threshold amount. Thus, in one example, the threshold amount may be based on an oxygen concentration indicating water at the oxygen sensor. Said another way, the threshold amount may be based on a decrease in oxygen concentration due to water at the oxygen sensor. Additionally, the threshold pumping current may be based on the location of the oxygen sensor, as determined by method 300.

If heater power does not increase by the threshold power and the pumping current does not decrease by the threshold pumping current, the controller maintains heater operation at 208. Specifically, at 208, the controller may maintain the heater power of the heating element according to the heating element temperature and/or additional oxygen sensor controls. For example, the heater power may be controlled based on feedback from the closed loop temperature controller of the oxygen sensor. In one example, the temperature controller may be a PI controller that maintains the heating element temperature around set point temperature by adjusting heater power.

However, if the heater power increases by the threshold amount (of power) and/or the pumping current decreases by the threshold amount (of pumping current), the method continues on to 210 to indicate water at the oxygen sensor. The method then continues on to 212 to decrease the heater power to a lower threshold level. In one example, the lower threshold level may be a power level less than the baseline power level. The lower threshold level may be based on a power level which may not result in cracking of the heating element. In another example, the lower threshold level may be a power level of substantially zero such that the heater power is turned off. Thus, in one example, the controller may turn the heating element off such that no power heater power is output by the sensor. Further, the method at 212 may include turning off (e.g., overriding) the closed loop temperature controller of the oxygen sensor that adjusts heater power responsive to heating element temperature. In this way, the heater power may be decreased or turned off even though the temperature of the oxygen sensor (e.g., heating element) may be below the set point temperature. Thus, the heater power may not be controlled based on feedback from the closed loop temperature controller. Said another way, the heater power may be controlled independent of oxygen sensor temperature changes until the heating element temperature reaches the threshold temperature at 214.

At 214, the method includes determining if the heating element temperature is less than a threshold temperature and/or if the heater power has been decreased (or turned off) for a duration. In one example, the threshold temperature may be a threshold cracking temperature. Said another way, the threshold temperature may be based on a temperature above which the heating element may degrade or crack. Thus, when the heating element temperature is less than the threshold temperature, the method may continue on to 218 to increase the heater power or turn the heater power of the heating element back on. In another example, the method may continue on to 218 once the heating element temperature is below the threshold temperature for a first duration. In yet another example, the method at 214 may include determining if the heater power is off for a second duration. In some cases, the temperature of the heating element may not be able to be measured or estimated. In this case, the heater power may be turned back on or increased to a baseline power level after the second duration. The second duration may be pre-determined and may be based on a time to evaporate water at the heating element and/or reduce the temperature of the heating element below the threshold cracking temperature. If one or more of the conditions at 214 are met, the method continues on to 218 to increase the heater power back to the baseline power level. In some examples, the method at 218 may include turning the heater power back on if it was turned off at 212. In yet another example, the method at 218 may include gradually increasing the heater power to the baseline power level. If, at 214, the heating element temperature is not less than the threshold temperature and the heater power has not been decreased or turned off for the duration, the method continues on to 216 to maintain the heater power at the lower threshold power. The method then circles back to 214.

In some examples, method 200 may only be executed for an oxygen sensor positioned in an engine intake (e.g., downstream of the CAC) when the engine is fully warmed up and engine temperatures are above a threshold temperature. Thus, during a cold start condition, method 200 may only be executed for an oxygen sensor positioned in an engine exhaust (e.g., exhaust oxygen sensor) and not for an oxygen sensor positioned in the engine intake (e.g., intake oxygen sensor). In yet other examples, method 200 may be executed for both intake oxygen sensors and exhaust oxygen sensors during both cold start and fully warmed up engine operation. However, the parameters used in method 200 (e.g., duration and thresholds) may be different for the intake oxygen sensor and the exhaust oxygen sensor.

FIG. 4 shows a graphical example of adjusting heater power of an oxygen sensor based on water at the oxygen sensor. As discussed above, the oxygen sensor includes a heating element with adjustable heater power. Specifically, graph 400 shows changes in heating element temperature of the oxygen sensor at plot 402, changes in heater power of the heating element at plot 404, changes in pumping current of the oxygen sensor at plot 406, and water at the oxygen sensor (e.g., water splashing against the oxygen sensor) at plot 408. In one example, the oxygen sensor may be an exhaust gas oxygen sensor positioned in an engine exhaust passage. In another example, the oxygen sensor may be an intake oxygen sensor positioned in an engine intake passage (such as in the intake passage, downstream of the CAC).

Prior to time t1, the heating element temperature may be around the set point temperature 410 (plot 402). The heater power may be around the baseline power level, $P_{base}$ (plot 404). Additionally, the pumping current of the oxygen sensor may be at a first level (plot 406). The first level may be a level at which little or no water is indicated at the oxygen sensor. In some examples, the first level may correspond to an oxygen concentration level under dry conditions.

At time t1, water may splash against the oxygen sensor and contact the heating element (indicated at plot 408). In response to water contacting the heating element, the heating element temperature decreases below the set point temperature (plot 402). In response, the heater power may increase by a first threshold amount (indicated at 412) to a higher threshold power level $P_{thresh}$ (e.g., higher than $P_{base}$). In one example, the $P_{thresh}$ may be a maximum power level of the heating element. At the same time, pumping current of the oxygen sensor may decrease by a second threshold amount (indicated at 416). If the heater power continued to be controlled based on heating element temperature (and the closed loop temperature controller of the sensor), the heater power may be maintained at $P_{thresh}$ between time t1 and almost time t3, as shown at plot 420. The heating element temperature may then increase as shown at plot 418. After increasing back to the set point temperature 410, the temperature may fluctuate since water may still be in the protection tube (e.g., chamber) and contacting the heating element. Due to maintaining the heater power around $P_{thresh}$, the heating element may crack around time t2, as indicated at 422 (plot 420).

Instead, in response to the pumping current decreasing by the second threshold amount (plot 408) and/or the heater power increasing by the first threshold amount (plot 404), the controller decreases the heater power below the baseline power level (plot 408). In some examples, as shown in graph 400, the controller may decrease the heater power to substantially zero such that the heating element is turned off.

In some examples, the heating element may be turned off (or the heater power decreased to a lower threshold level) for a duration, d1. The duration d1 may be pre-determined and based on a time to evaporate the water from the sensor and decrease the heating element temperature. In another example, the heating element may be turned off until the heating element temperature decreases to or below a threshold temperature 414. As shown at time t2, the heating element temperature reaches the threshold temperature 414. As discussed above, the threshold temperature 414 may be a threshold cracking temperature. In response, the heater power may be turned back on at time t2. The heater power is then increased to the baseline power level, $P_{base}$ (plot 404). There may be a lag between when the heater power is turned back on and the heating element temperature increases. As shown in FIG. 4, at time t3, the heating element temperature increases back to the set point temperature 410. In some examples, the heater power may be gradually increased back to the baseline power level at time t2, such that the heater power does not reach the baseline power level until time t3.

As shown at time t1 in FIG. 4, an engine method may include decreasing heater power of a heating element of an oxygen sensor in response to an increase in the heater power above a baseline power level by a threshold amount. Subsequently, as shown at time t2, the engine method may include increasing heater power to the baseline power level only after a temperature of the heating element decreases below a threshold temperature. In one example, decreasing the heater power includes turning off the heater power. In another example, decreasing the heater power includes decreasing the heater power to a lower threshold level, the lower threshold level less than the baseline power level.

The method further includes, when the temperature of the heating element cannot be determined, decreasing the heater power for a duration (e.g., d1 in FIG. 4), the duration pre-determined based on a time to evaporate water from the heating element, and then increasing the heater power back to the baseline power level. The threshold temperature is based on a temperature above which the heating element may crack (e.g., degrade) in the presence of water. As shown at plot 406, the method may further include decreasing the heater power of the heating element in response to a decrease in pumping current by a threshold amount, the threshold amount based on a decrease in oxygen concentration due to water at the oxygen sensor. Additionally, during the decreasing the heater power, the method may include disabling a closed loop temperature controller of the oxygen sensor.

Additionally, the oxygen sensor discussed in FIG. 4 may be an intake oxygen sensor positioned downstream of a charge air cooler. In this example, decreasing the heater power in response to the increase in the heater power above the baseline power level includes decreasing the heater power during engine operation when the engine is fully warmed up.

In this way, a method may include adjusting heater power of a heating element of an oxygen sensor when water is indicated at the oxygen sensor. In one example, water may be indicated at the oxygen sensor responsive to an increase in heater power above a baseline power level. In another example, water may be indicated at the oxygen sensor responsive to a decrease in pumping current of the oxygen sensor. When water is indicated at the oxygen sensor, the heater power may be decreased from an initial higher level to a second lower level. In some examples, the heater power may be turned off for a duration until water has evaporated from the oxygen sensor and the heating element temperature is below a threshold temperature. As such, a technical effect is achieved by reducing heater power of the heating element responsive an indication of water at the oxygen sensor. In this way, degradation of the oxygen sensor via heating element cracking may be reduced.

Note that the example control and estimation routines included herein can be used with various engine and/or vehicle system configurations. The control methods and routines disclosed herein may be stored as executable instructions in non-transitory memory. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. An engine method, comprising:
reducing heater power of an oxygen sensor heating element in response to an increase in the heater power by a threshold amount; and
adjusting the heater power of the heating element in response to a decrease in pumping current of the oxygen sensor by a threshold amount, the threshold amount based on an oxygen concentration indicating water at the oxygen sensor.

2. The method of claim 1, further comprising indicating water droplets at the oxygen sensor when the heater power increases above a baseline power level by the threshold amount.

3. The method of claim 1, wherein reducing the heater power of the heating element includes decreasing the heater power from an increased, first level due to water droplets hitting the heating element and to a second level, the second level lower than the first level and lower than a baseline power level.

4. The method of claim 3, wherein the second level is substantially zero such that the heater power is turned off.

5. The method of claim 3, further comprising, after decreasing the heater power, increasing the heater power to the baseline power level in response to a temperature of the heating element decreasing below a threshold temperature, the threshold temperature based on a temperature at which the heating element may crack under water splash conditions.

6. The method of claim 3, further comprising, after decreasing the heater power, increasing the heater power to the baseline power level after a duration, the duration based on a time to evaporate water at the heating element and reduce a temperature of the heating element below a threshold cracking temperature.

7. The method of claim 1, wherein the oxygen sensor is one of an exhaust oxygen sensor positioned in an engine exhaust or an intake oxygen sensor positioned in an engine intake.

8. A method for an engine, comprising:
decreasing heater power of a heating element of an oxygen sensor in response to an increase in the heater power above a baseline power level by a threshold amount;
subsequently increasing the heater power to the baseline power level only after a temperature of the heating element decreases below a threshold temperature; and
decreasing the heater power in response to a decrease in pumping current by a threshold amount, the threshold amount based on a decrease in oxygen concentration due to water at the oxygen sensor.

9. The method of claim 8, wherein decreasing the heater power includes one of turning off the heater power or decreasing the heater power to a lower threshold level, the lower threshold level less than the baseline power level.

10. The method of claim 8, further comprising, when the temperature of the heating element cannot be determined, decreasing the heater power for a duration, the duration pre-determined based on a time to evaporate water from the heating element, and then increasing the heater power back to the baseline power level.

11. The method of claim 8, wherein the threshold temperature is based on a temperature above which the heating element may crack.

12. The method of claim 8, further comprising, during the decreasing the heater power, disabling a closed loop temperature controller of the oxygen sensor.

13. The method of claim 8, wherein the oxygen sensor is an intake oxygen sensor positioned downstream of a charge air cooler and upstream of engine cylinders and wherein the decreasing the heater power in response to the increase in the heater power above the baseline power level includes decreasing the heater power during engine operation when the engine is fully warmed up.

14. A system for an engine, comprising:
an intake manifold including an intake throttle;

a charge air cooler positioned upstream of the intake manifold;

a first oxygen sensor positioned at an outlet of the charge air cooler, the first oxygen sensor including a first heating element; and a controller with computer readable instructions for turning off heater power of the first heating element in response to an indication of water contacting the first oxygen sensor, wherein water contacting the first oxygen sensor is indicated by one or more of an increase in heater power of the first heating element above a baseline power level by a first threshold amount or a decrease in pumping current of the first oxygen sensor by a second threshold amount.

15. The system of claim 14, wherein the computer readable instructions further include subsequently turning on the heater power after the heater power is turned off for a duration, the duration based on one or more of an amount of time for water to evaporate from the first heating element or an amount of time to reduce a temperature of the first heating element below a threshold cracking temperature.

16. The system of claim 14, further comprising a second oxygen sensor positioned in an exhaust passage of the engine, the second oxygen sensor including a second heating element.

17. The system of claim 16, wherein the computer readable instructions further include instructions for turning off heater power of the second heating element in response to an indication of water contacting the second oxygen sensor and wherein water contacting the second oxygen sensor is indicated by one or more of an increase in heater power of the second heating element above a baseline power level by a first threshold amount or a decrease in pumping current of the second oxygen sensor by a second threshold amount.

* * * * *